United States Patent
Zones et al.

(10) Patent No.: US 7,084,304 B2
(45) Date of Patent: Aug. 1, 2006

(54) ACYLATION USING MOLECULAR SIEVE SSZ-70

(75) Inventors: Stacey I. Zones, San Francisco, CA (US); Allen W. Burton, Jr., Richmond, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 11/266,112

(22) Filed: Nov. 2, 2005

(65) Prior Publication Data

US 2006/0142617 A1 Jun. 29, 2006

Related U.S. Application Data

(60) Provisional application No. 60/639,215, filed on Dec. 23, 2004.

(51) Int. Cl.
*C07C 2/66* (2006.01)
*C07C 2/86* (2006.01)
*C07C 45/46* (2006.01)

(52) U.S. Cl. ............ 568/309; 568/319; 568/331; 568/335; 585/467

(58) Field of Classification Search ............ 585/467, 585/309, 319, 331, 335
See application file for complete search history.

(56) References Cited

U.S. PATENT DOCUMENTS

| | | | | |
|---|---|---|---|---|
| 4,826,667 A | * | 5/1989 | Zones et al. | 423/706 |
| 5,173,281 A | * | 12/1992 | Chang et al. | 423/702 |
| 5,278,116 A | * | 1/1994 | Kresge et al. | 502/84 |
| 5,362,697 A | * | 11/1994 | Fung et al. | 502/71 |
| 6,136,290 A | * | 10/2000 | Benazzi et al. | 423/705 |
| 6,630,606 B1 | * | 10/2003 | Poliakoff et al. | 568/309 |

* cited by examiner

*Primary Examiner*—David Sample
(74) *Attorney, Agent, or Firm*—Richard J. Sheridan

(57) ABSTRACT

The present invention relates to new crystalline molecular sieve SSZ-70 prepared using a N,N'-diisopropyl imidazolium cation as a structure-directing agent, methods for synthesizing SSZ-70 and processes employing SSZ-70 in a catalyst.

4 Claims, 2 Drawing Sheets

CALCINED SSZ-70

AS-SYNTHESIZED SSZ-70

ACYLATION USING MOLECULAR SIEVE SSZ-70

This application claims benefit under 35 USC 119 of Provisional Application 60/639,215, filed Dec. 23, 2004.

BACKGROUND OF THE INVENTION

1. Field of the Invention

The present invention relates to new crystalline molecular sieve SSZ-70, a method for preparing SSZ-70 using a N,N'-diisopropyl imidazolium cation as a structure directing agent and the use of SSZ-70 in catalysts for, e.g., hydrocarbon conversion reactions.

2. State of the Art

Because of their unique sieving characteristics, as well as their catalytic properties, crystalline molecular sieves and zeolites are especially useful in applications such as hydrocarbon conversion, gas drying and separation. Although many different crystalline molecular sieves have been disclosed, there is a continuing need for new zeolites with desirable properties for gas separation and drying, hydrocarbon and chemical conversions, and other applications. New zeolites may contain novel internal pore architectures, providing enhanced selectivities in these processes.

Crystalline aluminosilicates are usually prepared from aqueous reaction mixtures containing alkali or alkaline earth metal oxides, silica, and alumina. Crystalline borosilicates are usually prepared under similar reaction conditions except that boron is used in place of aluminum. By varying the synthesis conditions and the composition of the reaction mixture, different zeolites can often be formed.

SUMMARY OF THE INVENTION

The present invention is directed to a family of crystalline molecular sieves with unique properties, referred to herein as "molecular sieve SSZ-70" or simply "SSZ-70". Preferably, SSZ-70 is obtained in its silicate, aluminosilicate, titanosilicate, vanadosilicate or borosilicate form. The term "silicate" refers to a molecular sieve having a high mole ratio of silicon oxide relative to aluminum oxide, preferably a mole ratio greater than 100, including molecular sieves comprised entirely of silicon oxide. As used herein, the term "aluminosilicate" refers to a molecular sieve containing both aluminum oxide and silicon oxide and the term "borosilicate" refers to a molecular sieve containing oxides of both boron and silicon.

In accordance with this invention, there is provided a method for performing an acylation reaction on an aromatic substrate $ArH_n$ to form a product $ArH_{n-1}COR$, the method comprising the steps of:

providing the aromatic substrate, intimately mixing the substrate and an acylating agent, wherein the acylating agent is selected from the group consisting of a carboxylic acid derivative, a carboxylic acid, an acid anhydride, an ester, and an acyl halide, and exposing an intimate mixture thus formed to a catalyst comprising a molecular sieve having a mole ratio greater than about 15 of (1) silicon oxide to (2) an oxide selected from aluminum oxide, gallium oxide, iron oxide, boron oxide, titanium oxide, vanadium oxide and mixtures thereof and having, after calcination, the X-ray diffraction lines of Table II. It should be noted that the mole ratio of oxide (1) to oxide (2) can be infinity, i.e., there is no oxide (2) in the molecular sieve. In these cases, the molecular sieve is an essentially all-silica molecular sieve.

The present invention also includes the acylation reaction wherein the molecular sieve is predominantly in the hydrogen form, which hydrogen form is prepared by ion exchanging with an acid or with a solution of an ammonium salt followed by a second calcination. If the molecular sieve is synthesized with a high enough ratio of structure directing agent ("SDA") cation to sodium ion, calcination alone may be sufficient. For high catalytic activity, the SSZ-70 molecular sieve may be predominantly in its hydrogen ion form. As used herein, "predominantly in the hydrogen form" means that, after calcination, at least 80% of the cation sites are occupied by hydrogen ions and/or rare earth ions.

DETAILED DESCRIPTION OF THE INVENTION

Figure 1:
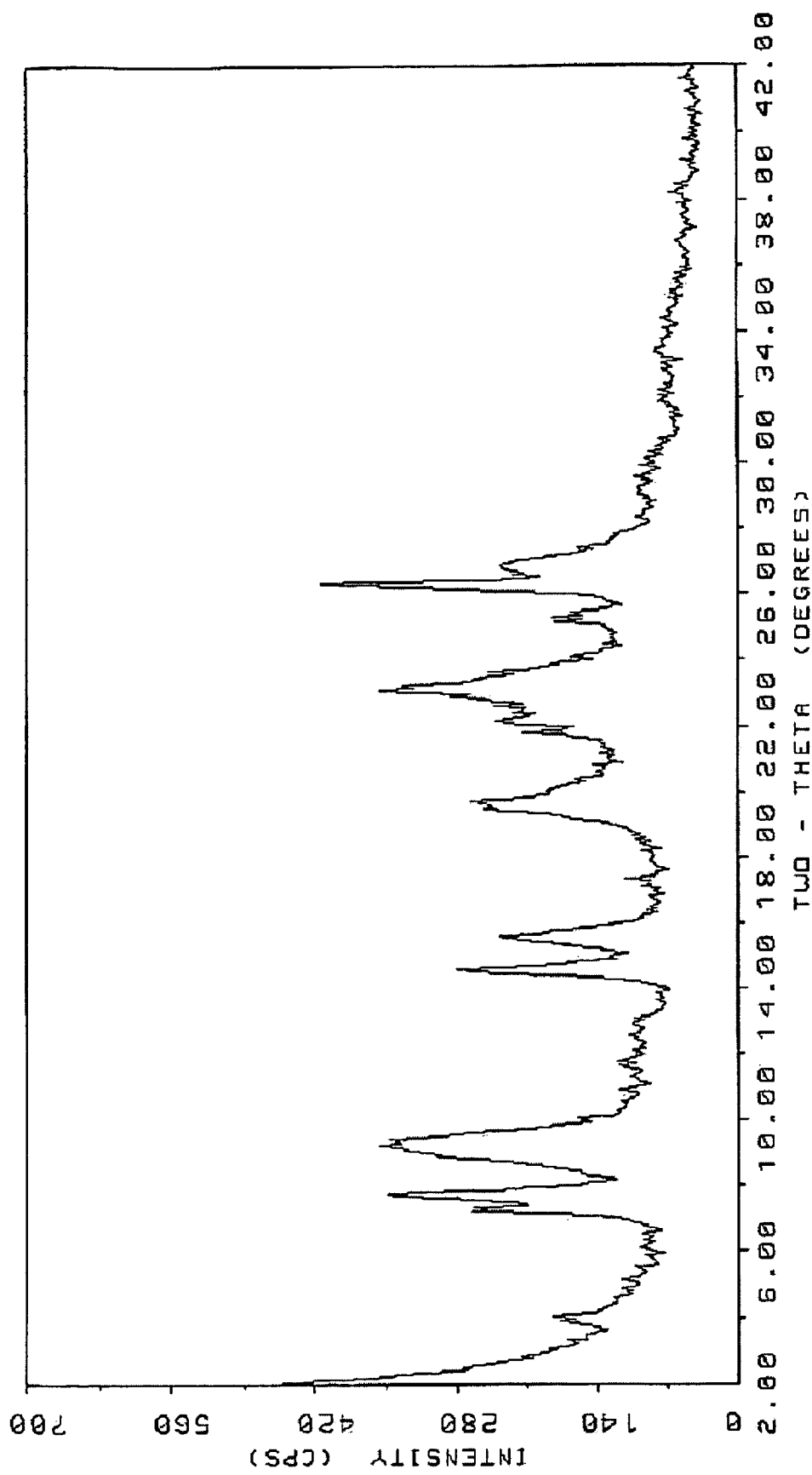
FIG. 1 is an X-ray diffraction pattern of SSZ-70 after it has been calcined.
Figure 2:
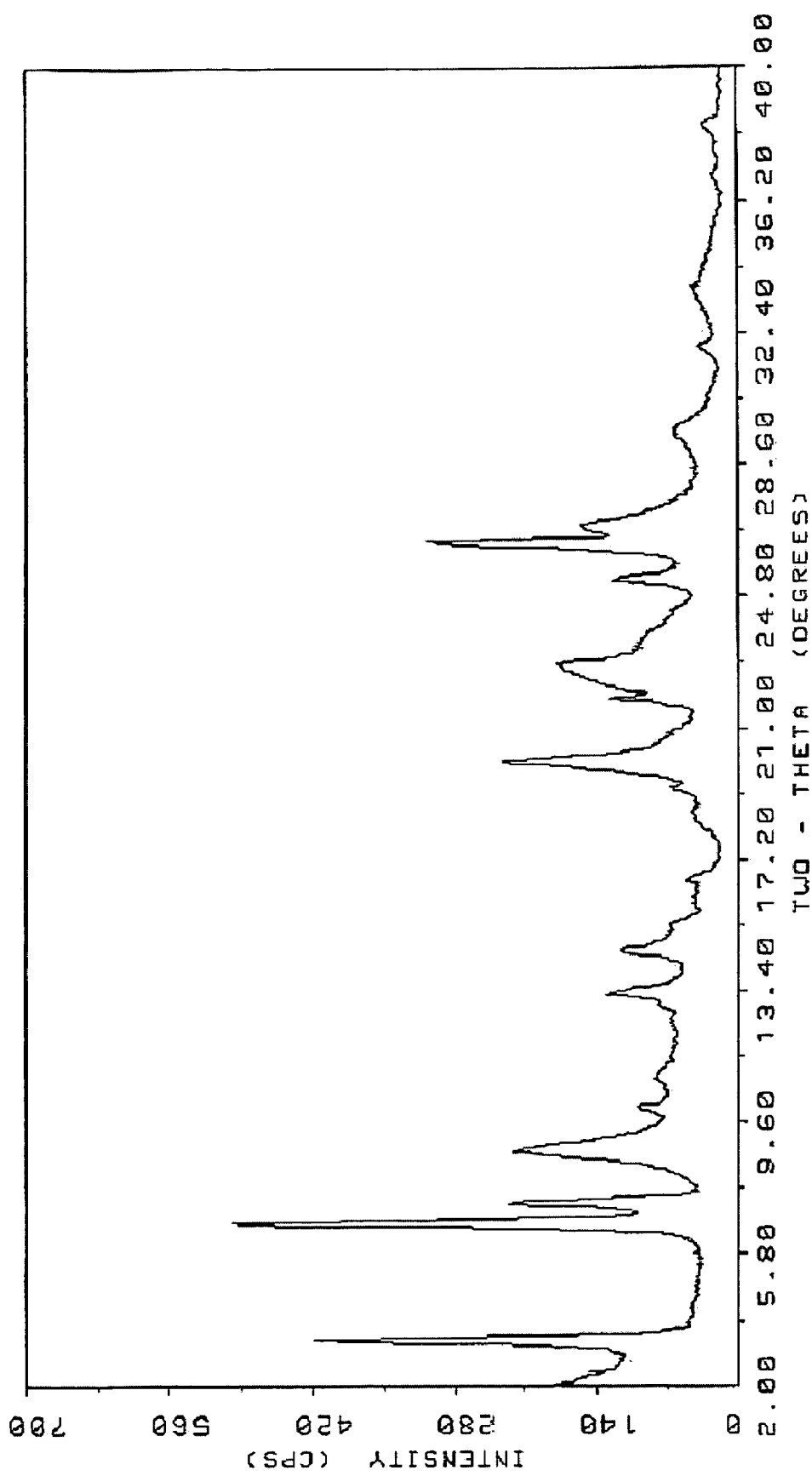
FIG. 2 is an X-ray diffraction pattern of SSZ-70 in the as-synthesized form, i.e., prior to calcination with the SDA still in the pores of the SSZ-70.

The present invention comprises a family of crystalline molecular sieves designated herein "molecular sieve SSZ-70" or simply "SSZ-70". In preparing SSZ-70, a N,N'-diisopropyl imidazolium cation (referred to herein as "DIPI") is used as a structure directing agent ("SDA"), also known as a crystallization template. The SDA useful for making SSZ-70 has the following structure:

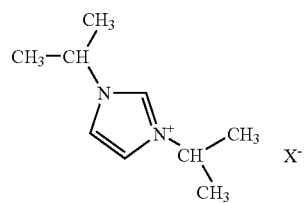

The SDA cation is associated with an anion ($X^-$) which may be any anion that is not detrimental to the formation of the molecular sieve. Representative anions include halogen, e.g., fluoride, chloride, bromide and iodide, hydroxide, acetate, sulfate, tetrafluoroborate, carboxylate, and the like. Hydroxide is the most preferred anion.

SSZ-70 is prepared from a reaction mixture having the composition shown in Table A below.

TABLE A

| | Reaction Mixture | |
|---|---|---|
| | Typical | Preferred |
| $YO_2/B_2O_3$ | 5–60 | 10–60 |
| $OH^-/YO_2$ | 0.10–0.50 | 0.20–0.30 |
| $Q/YO_2$ | 0.05–0.50 | 0.10–0.20 |
| $M_{2/n}/YO_2$ | 0–0.40 | 0.10–0.25 |
| $H_2O/YO_2$ | 30–80 | 35–45 |
| $F/YO_2$ | 0–0.50 | 0 | where Y is silicon; M is an alkali metal cation, alkaline earth metal cation or mixtures thereof; n is the valence of M (i.e., 1 or 2); F is fluorine and Q is a N,N'-diisopropyl imidazolium cation.

In practice, SSZ-70 is prepared by a process comprising:

(a) preparing an aqueous solution containing sources of at least two oxides capable of forming a crystalline molecular sieve and a DIPI cation having an anionic counterion which is not detrimental to the formation of SSZ-70;

(b) maintaining the aqueous solution under conditions sufficient to form crystals of SSZ-70; and (c) recovering the crystals of SSZ-70.

Accordingly, SSZ-70 may comprise the crystalline material and the SDA in combination with metallic and non-metallic oxides bonded in tetrahedral coordination through shared oxygen atoms to form a cross-linked three dimensional crystal structure. Typical sources of silicon oxide include silicates, silica hydrogel, silicic acid, fumed silica, colloidal silica, tetra-alkyl orthosilicates, and silica hydroxides. Boron can be added in forms corresponding to its silicon counterpart, such as boric acid.

A source zeolite reagent may provide a source of boron. In most cases, the source zeolite also provides a source of silica. The source zeolite in its deboronated form may also be used as a source of silica, with additional silicon added using, for example, the conventional sources listed above. Use of a source zeolite reagent for the present process is more completely described in U.S. Pat. No. 5,225,179, issued Jul. 6, 1993 to Nakagawa entitled "Method of Making Molecular Sieves", the disclosure of which is incorporated herein by reference.

Typically, an alkali metal hydroxide and/or an alkaline earth metal hydroxide, such as the hydroxide of sodium, potassium, lithium, cesium, rubidium, calcium, and magnesium, is used in the reaction mixture; however, this component can be omitted so long as the equivalent basicity is maintained. The SDA may be used to provide hydroxide ion. Thus, it may be beneficial to ion exchange, for example, the halide to hydroxide ion, thereby reducing or eliminating the alkali metal hydroxide quantity required. The alkali metal cation or alkaline earth cation may be part of the as-synthesized crystalline oxide material, in order to balance valence electron charges therein.

The reaction may also be carried out using HF to counterbalance the OH-contribution from the SDA, and run the synthesis in the absence of alkali cations. Running in the absence of alkali cations has the advantage of being able to prepare a catalyst from the synthesis product, by using calcination alone, i.e., no ion-exchange step (to remove alkali or alkaline earth cations) is necessary. In using HF, the reaction operates best when both the SDA and HF have mole ratios of 0.50 relative to $YO_2$ (e.g., silica).

The reaction mixture is maintained at an elevated temperature until the crystals of the SSZ-70 are formed. The hydrothermal crystallization is usually conducted under autogenous pressure, at a temperature between 100° C. and 200° C., preferably between 135° C. and 160° C. The crystallization period is typically greater than 1 day and preferably from about 3 days to about 20 days.

Preferably, the molecular sieve is prepared using mild stirring or agitation.

During the hydrothermal crystallization step, the SSZ-70 crystals can be allowed to nucleate spontaneously from the reaction mixture. The use of SSZ-70 crystals as seed material can be advantageous in decreasing the time necessary for complete crystallization to occur. In addition, seeding can lead to an increased purity of the product obtained by promoting the nucleation and/or formation of SSZ-70 over any undesired phases. When used as seeds, SSZ-70 crystals are added in an amount between 0.1 and 10% of the weight of first tetravalent element oxide, e.g. silica, used in the reaction mixture.

Once the molecular sieve crystals have formed, the solid product is separated from the reaction mixture by standard mechanical separation techniques such as filtration. The crystals are water-washed and then dried, e.g., at 90° C. to 150° C. for from 8 to 24 hours, to obtain the as-synthesized SSZ-70 crystals. The drying step can be performed at atmospheric pressure or under vacuum.

SSZ-70 as prepared has a mole ratio of (1) silicon oxide to (2) boron oxide greater than about 15; and has, after calcination, the X-ray diffraction lines of Table II below. SSZ-70 further has a composition, as synthesized (i.e., prior to removal of the SDA from the SSZ-70) and in the anhydrous state, in terms of mole ratios, shown in Table B below.

TABLE B

| As-Synthesized SSZ-70 | |
| --- | --- |
| $YO_2/B_2O_3$ | 20–60 |
| $M_{2/n}/YO_2$ | 0–0.03 |
| $Q/YO_2$ | 0.02–0.05 |
| $F/YO_2$ | 0–0.10 | where Y, M, n, F and Q are as defined above.

SSZ-70 can be an essentially all-silica material. As used herein, "essentially all-silica" means that the molecular sieve is comprised of only silicon oxide or is comprised of silicon oxide and only trace amounts of other oxides, such as aluminum oxide, which may be introduced as impurities in the source of silicon oxide. Thus, in a typical case where oxides of silicon and boron are used, SSZ-70 can be made essentially boron free, i.e., having a silica to boron oxide mole ratio of ∞. SSZ-70 is made as a borosilicate and then the boron can then be removed, if desired, by treating the borosilicate SSZ-70 with acetic acid at elevated temperature (as described in Jones et al., Chem. Mater., 2001, 13, 1041–1050) to produce an essentially all-silica version of SSZ-70.

If desired, SSZ-70 can be made as a borosilicate and then the boron can be removed as described above and replaced with metal atoms by techniques known in the art. Aluminum, gallium, iron, titanium, vanadium and mixtures thereof can be added in this manner.

It is believed that SSZ-70 is comprised of a new framework structure or topology which is characterized by its X-ray diffraction pattern. SSZ-70, as-synthesized, has a crystalline structure whose X-ray powder diffraction pattern exhibit the characteristic lines shown in Table I and is thereby distinguished from other molecular sieves.

TABLE I

| As-Synthesized SSZ-70 | | |
| --- | --- | --- |
| 2 Theta[a] | d-spacing (Angstroms) | Relative Intensity (%)[b] |
| 3.32 | 26.6 | VS |
| 6.70 | 13.2 | VS |
| 7.26 | 12.2 | S |
| 8.78 | 10.1 | S |
| 13.34 | 6.64 | M |
| 20.02 | 4.44 | S |

TABLE I-continued

As-Synthesized SSZ-70

| 2 Theta[a] | d-spacing (Angstroms) | Relative Intensity (%)[b] |
|---|---|---|
| 22.54 | 3.94 | M |
| 22.88 | 3.89 | M |
| 26.36 | 3.38 | S–VS |
| 26.88 | 3.32 | M |

[a] ± 0.15
[b] The X-ray patterns provided are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.

Table IA below shows the X-ray powder diffraction lines for as-synthesized SSZ-70 including actual relative intensities.

TABLE IA

| 2 Theta[a] | d-spacing (Angstroms) | Relative Intensity (%) |
|---|---|---|
| 3.32 | 26.6 | 84 |
| 6.70 | 13.2 | 100 |
| 7.26 | 12.2 | 45 |
| 8.78 | 10.1 | 44 |
| 13.34 | 6.64 | 26 |
| 20.02 | 4.44 | 46 |
| 22.54 | 3.94 | 33 |
| 22.88 | 3.89 | 36 |
| 26.36 | 3.38 | 61 |
| 26.88 | 3.32 | 31 |

[a] ± 0.15

After calcination, the SSZ-70 molecular sieves have a crystalline structure whose X-ray powder diffraction pattern include the characteristic lines shown in Table II:

TABLE II

Calcined SSZ-70

| 2 Theta[a] | d-spacing (Angstroms) | Relative Intensity (%) |
|---|---|---|
| 7.31 | 12.1 | VS |
| 7.75 | 11.4 | VS |
| 9.25 | 9.6 | VS |
| 14.56 | 6.08 | VS |
| 15.61 | 5.68 | S |
| 19.60 | 4.53 | S |
| 21.81 | 4.07 | M |
| 22.24 | 4.00 | M–S |
| 26.30 | 3.39 | VS |
| 26.81 | 3.33 | VS |

[a] ± 0.15

Table IIA below shows the X-ray powder diffraction lines for calcined SSZ-70 including actual relative intensities.

TABLE IIA

| 2 Theta[a] | d-spacing (Angstroms) | Relative Intensity (%) |
|---|---|---|
| 7.31 | 12.1 | 67 |
| 7.75 | 11.4 | 93 |
| 9.25 | 9.6 | 79 |
| 14.56 | 6.08 | 68 |
| 15.61 | 5.68 | 49 |
| 19.60 | 4.53 | 58 |
| 21.81 | 4.07 | 38 |
| 22.24 | 4.00 | 41 |
| 26.30 | 3.39 | 99 |
| 26.81 | 3.33 | 80 |

[a] ± 0.15

The X-ray powder diffraction patterns were determined by standard techniques. The radiation was the K-alpha/doublet of copper. The peak heights and the positions, as a function of 2θ where θ is the Bragg angle, were read from the relative intensities of the peaks, and d, the interplanar spacing in Angstroms corresponding to the recorded lines, can be calculated.

The variation in the scattering angle (two theta) measurements, due to instrument error and to differences between individual samples, is estimated at ±0.15 degrees.

The X-ray diffraction pattern of Table I is representative of "as-synthesized" or "as-made" SSZ-70 molecular sieves. Minor variations in the diffraction pattern can result from variations in the silica-to-boron mole ratio of the particular sample due to changes in lattice constants. In addition, sufficiently small crystals will affect the shape and intensity of peaks, leading to significant peak broadening.

Representative peaks from the X-ray diffraction pattern of calcined SSZ-70 are shown in Table II. Calcination can also result in changes in the intensities of the peaks as compared to patterns of the "as-made" material, as well as minor shifts in the diffraction pattern. The molecular sieve produced by exchanging the metal or other cations present in the molecular sieve with various other cations (such as $H^+$ or $NH_4^+$) yields essentially the same diffraction pattern, although again, there may be minor shifts in the interplanar spacing and variations in the relative intensities of the peaks. Notwithstanding these minor perturbations, the basic crystal lattice remains unchanged by these treatments.

Crystalline SSZ-70 can be used as-synthesized, but preferably will be thermally treated (calcined). Usually, it is desirable to remove the alkali metal cation by ion exchange and replace it with hydrogen, ammonium, or any desired metal ion. The molecular sieve can be leached with chelating agents, e.g., EDTA or dilute acid solutions, to increase the silica to alumina mole ratio. The molecular sieve can also be steamed; steaming helps stabilize the crystalline lattice to attack from acids.

The molecular sieve can be used in intimate combination with hydrogenating components, such as tungsten, vanadium, molybdenum, rhenium, nickel, cobalt, chromium, manganese, or a noble metal, such as palladium or platinum, for those applications in which a hydrogenation-dehydrogenation function is desired.

Metals may also be introduced into the molecular sieve by replacing some of the cations in the molecular sieve with metal cations via standard ion exchange techniques (see, for example, U.S. Pat. No. 3,140,249 issued Jul. 7, 1964 to Plank et al.; U.S. Pat. No. 3,140,251 issued Jul. 7, 1964 to Plank et al.; and U.S. Pat. No. 3,140,253 issued Jul. 7, 1964 to Plank et al.). Typical replacing cations can include metal cations, e.g., rare earth, Group IA, Group IIA and Group VIII metals, as well as their mixtures. Of the replacing metallic cations, cations of metals such as rare earth, Mn, Ca, Mg, Zn, Cd, Pt, Pd, Ni, Co, Ti, Al, Sn, and Fe are particularly preferred.

The hydrogen, ammonium, and metal components can be ion-exchanged into the SSZ-70. The SSZ-70 can also be impregnated with the metals, or the metals can be physically and intimately admixed with the SSZ-70 using standard methods known to the art.

Typical ion-exchange techniques involve contacting the synthetic molecular sieve with a solution containing a salt of the desired replacing cation or cations. Although a wide variety of salts can be employed, chlorides and other halides, acetates, nitrates, and sulfates are particularly preferred. The molecular sieve is usually calcined prior to the ion-exchange procedure to remove the organic matter present in the channels and on the surface, since this results in a more effective ion exchange. Representative ion exchange techniques are disclosed in a wide variety of patents including U.S. Pat. No. 3,140,249 issued on Jul. 7, 1964 to Plank et al.; U.S. Pat. No. 3,140,251 issued on Jul. 7, 1964 to Plank et al.; and U.S. Pat. No. 3,140,253 issued on Jul. 7, 1964 to Plank et al.

Following contact with the salt solution of the desired replacing cation, the molecular sieve is typically washed with water and dried at temperatures ranging from 65° C. to about 200° C. After washing, the molecular sieve can be calcined in air or inert gas at temperatures ranging from about 200° C. to about 800° C. for periods of time ranging from 1 to 48 hours, or more, to produce a catalytically active product especially useful in hydrocarbon conversion processes.

Regardless of the cations present in the synthesized form of SSZ-70, the spatial arrangement of the atoms which form the basic crystal lattice of the molecular sieve remains essentially unchanged.

SSZ-70 can be formed into a wide variety of physical shapes. Generally speaking, the molecular sieve can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the SSZ-70 can be extruded before drying, or, dried or partially dried and then extruded.

SSZ-70 can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa, both of which are incorporated by reference herein in their entirety.

The molecular sieve of the present invention can be used in a catalyst for acylating an aromatic substrate $ArH_n$, where n is at least 1, by reacting the aromatic substrate with an acylating agent in the presence of the catalyst. The product of the acylation reaction is $ArH_{n-1}COR$ where R is an organic radical.

Examples of the aromatic substrate include, but are not limited to, benzene, toluene, anisole and 2-naphthol. Examples of the acylating agent included, but are not limited to, carboxylic acid derivatives, carboxylic acids, acid anhydrides, esters, and acyl halides.

Reaction conditions are known in the art (see, for example, U.S. Pat. No. 6,630,606, issued Oct. 7, 2003 to Poliakoff et al., U.S. Pat. No. 6,459,000, issued Oct. 1, 2002 to Choudhary et al., and U.S. Pat. No. 6,548,722, issued Apr. 15, 2003 to Choudhary et al., all of which are incorporated herein by reference in their entirety). Typically, the acylation reaction is conducted with a weight ratio of the catalyst to the acylating agent of about 0.03 to about 0.5, a mole ratio of aromatic substrate to acylating agent of about 1.0 to about 20, a reaction temperature in the range of about 20° C. to about 200° C., a reaction pressure in the range of about 1 atm to about 5 atm, and a reaction time of about 0.05 hours to about 20 hours.

EXAMPLES

The following examples demonstrate but do not limit the present invention.

Examples 1–6

Synthesis of Borosilicate SSZ-70 (B-SSZ-70)

B-SSZ-70 is synthesized by preparing the gel compositions, i.e., reaction mixtures, having the compositions, in terms of mole ratios, shown in the table below. The resulting gel is placed in a Parr bomb reactor and heated in an oven at the temperature (° C.) indicated in the table while rotating at 43 rpm. Amounts in the table are in millimoles. Products are analyzed by X-ray diffraction (XRD) and found to be B-SSZ-70 or a mixture of B-SSZ-70 and amorphous material.

| Ex. No. | $SiO_2$ | DIPI | $H_2O/SiO_2$ | HF | $H_3BO_3$ | Temp., ° C. | Seeds | Days | Prod. |
|---|---|---|---|---|---|---|---|---|---|
| 1 | 18 | 9 | 15 | 9 | 1.0 | 150 | No | 95 | AM/B-SSZ-70 |
| 2 | 18 | 9 | 15 | 9 | 1.0 | 150 | Yes | 98 | AM/B-SSZ-70 |
| 3 | 18 | 9 | 15 | 9 | 1.0 | 170 | No | 52 | B-SSZ-70 |
| 4 | 18 | 9 | 15 | 9 | 1.0 | 150 | Yes | 80 | B-SSZ-70 |
| 5 | 18 | 9 | 15 | 9 | 3.3 | 170 | No | 52 | B-SSZ-70 |
| 6 | 18 | 9 | 15 | 9 | 5.0 | 170 | No | 61 | B-SSZ-70 |

AM = amorphous material

The X-ray diffraction lines for as-synthesized SSZ-70 are shown in the table below.

| As-Synthesized SSZ-70 XRD | | |
|---|---|---|
| 2 Theta[a] | d-spacing (Angstroms) | Relative Intensity (%) |
| 3.32 | 26.6 | 84 |
| 6.70 | 13.2 | 100 |
| 7.26 | 12.2 | 45 |
| 8.78 | 10.1 | 44 |
| 10.04 | 8.81 | 20 |
| 10.88 | 8.13 | 17 |
| 13.00 | 6.81 | 16 |
| 13.34 | 6.64 | 26 |
| 14.60 | 6.07 | 23 |
| 15.36 | 5.77 | 14 |
| 16.66 | 5.32 | 10 |
| 18.54 | 4.79 | 6 |
| 19.30 | 4.60 | 14 |
| 20.02 | 4.44 | 46 |
| 21.86 | 4.07 | 25 |
| 22.54 | 3.94 | 33 |
| 22.88 | 3.89 | 36 |
| 24.38 | 3.65 | 13 |
| 25.28 | 3.52 | 25 |
| 26.36 | 3.38 | 61 |

-continued

As-Synthesized SSZ-70 XRD

| 2 Theta[a] | d-spacing (Angstroms) | Relative Intensity (%) |
|---|---|---|
| 26.88 | 3.32 | 31 |
| 29.56 | 3.02 | 6 |
| 32.00 | 2.80 | 8 |
| 33.61 | 2.67 | 4 |
| 36.94 | 2.43 | 5 |
| 38.40 | 2.34 | 7 |

[a] ± 0.15

Example 7

A run is set up as in the table above but the mole ratios are as follows: $SiO_2$=16 mmoles, DIPI=5 mmoles, $H_3BO_3$=4 mmoles and water=240 mmoles. No HF component is used. The reaction is run for only seven days at 43 RPM at 170° C. The product is SSZ-70.

Example 8

Calcination of SSZ-70

SSZ-70 is calcined to remove the structure directing agent (SDA) as described below. A thin bed of SSZ-70 in a calcination dish is heated in a muffle furnace from room temperature to 120° C. at a rate of 1° C./minute and held for 2 hours. Then, the temperature is ramped up to 540° C. at a rate of 1° C./minute and held for 5 hours. The temperature is ramped up again at 1° C./minute to 595° C. and held there for 5 hours. A 50/50 mixture of air and nitrogen passes through the muffle furnace at a rate of 20 standard cubic feet (0.57 standard cubic meters) per minute during the calcination process. The XRD lines for calcined SSZ-70 are shown in the table below.

| 2 Theta[a] | d-spacing (Angstroms) | Relative Intensity (%) |
|---|---|---|
| 3.93 | 22.5 | 22 |
| 7.31 | 12.1 | 67 |
| 7.75 | 11.4 | 93 |
| 9.25 | 9.6 | 79 |
| 14.56 | 6.08 | 68 |
| 15.61 | 5.68 | 49 |
| 17.34 | 5.11 | 15 |
| 19.60 | 4.53 | 58 |
| 21.81 | 4.07 | 38 |
| 22.24 | 4.00 | 41 |
| 23.11 | 3.85 | 77 |
| 25.30 | 3.52 | 23 |
| 26.30 | 3.39 | 99 |
| 26.81 | 3.33 | 80 |

[a] ± 0.15

Example 9

Replacement of Boron with Aluminum

Calcined SSZ-70 (about 5 grams) is combined with 500 grams of 1 M aqueous $Al(NO_3)_3$ solution and treated under reflux for 100 hours. The resulting aluminum-containing SSZ-70 product is then washed with 100 ml 0.01N HCl and then with one liter of water, filtered and air dried at room temperature in a vacuum filter.

Example 10

Constraint Index

The hydrogen form of calcined SSZ-70 is pelletized at 3 KPSI, crushed and granulated to 20–40 mesh. A 0.6 gram sample of the granulated material is calcined in air at 540° C. for 4 hours and cooled in a desiccator to ensure dryness. Then, 0.5 gram is packed into a ⅜ inch stainless steel tube with alundum on both sides of the molecular sieve bed. A Lindburg furnace is used to heat the reactor tube. Helium is introduced into the reactor tube at 10 cc/min. and at atmospheric pressure. The reactor is heated to about 427° C. (800° F.), and a 50/50 feed of n-hexane and 3-methylpentane is introduced into the reactor at a rate of 8 µl/min. The feed is delivered by a Brownlee pump. Direct sampling into a GC begins after 10 minutes of feed introduction. The Constraint Index (CI) value is calculated from the GC data using methods known in the art. The results are shown in the table below.

| Time, Min. | 10 | 40 | 70 | 100 |
|---|---|---|---|---|
| Feed Conv. % | 6.4 | 6.5 | 6.5 | 6.4 |
| CI (excl. 2-MP) | 0.6 | 0.59 | 0.56 | 0.56 |
| CI (incl. 2-MP) | 0.78 | 0.79 | 0.75 | 0.76 |

2-MP = 2-methylpentane

Example 11

Hydrocracking of n-Hexadecane

A 1 gm sample of calcined SSZ-70 is suspended in 10 gm de-ionized water. To this suspension, a solution of $Pt(NH_3)_4$·$(NO_3)_2$ at a concentration which would provide 0.5 wt. % Pt with respect to the dry weight of the molecular sieve sample is added. The pH of the solution is adjusted to pH of ~9 by a drop-wise addition of dilute ammonium hydroxide solution. The mixture is then allowed to stand at 25° C. for 48 hours. The mixture is then filtered through a glass frit, washed with de-ionized water, and air-dried. The collected Pt-SSZ-70 sample is slowly calcined up to 288° C. in air and held there for three hours.

The calcined Pt/SSZ-70 catalyst is pelletized in a Carver Press and granulated to yield particles with a 20/40 mesh size. Sized catalyst (0.5 g) is packed into a ¼ inch OD tubing reactor in a micro unit for n-hexadecane hydroconversion. The table below gives the run conditions and the products data for the hydrocracking test on n-hexadecane.

The results shown in the table below show that SSZ-70 is effective as a hydrocracking catalyst. The data show that the catalyst has a very high selectivity for hydrocracking to linear paraffins, rather than isomerization selectivity. Also, a high ratio of liquid/gas ($C_{5+}/C_{4-}$) is achieved.

| Temperature | 660° F. (349° C.) | 690° F. (366° C.) |
|---|---|---|
| Time-on-Stream (hrs.) | 40 hours | 53 hours |
| PSIG | 2200 | 2200 |
| Titrated? | No | No |
| n-16, % Conversion | 52% | 89% |
| Isomerization Selectivity, % | 5.1 | 2.2 |
| $C_{5+}/C_{4-}$ | 11.5 | 7.0 |
| $C_4$–$C_{13}$ i/n | 0.02 | 0.03 |

Example 12

Micropore Volume

SSZ-70 has a micropore volume of 0.071 cc/gm based on argon adsorption isotherm at 87.5° K. (−186° C.) recorded on ASAP 2010 equipment from Micromerities. The sample is first degassed at 400° C. for 16 hours prior to argon adsorption. The low-pressure dose is 2.00 cm$^3$/g (STP). A maximum of one hour equilibration time per dose is used and the total run time is 37 hours. The argon adsorption isotherm is analyzed using the density function theory (DFT) formalism and parameters developed for activated carbon slits by Olivier (*Porous Mater.* 1995, 2, 9) using the Saito Foley adaptation of the Horvarth-Kawazoe formalism (*Microporous Materials,* 1995, 3, 531) and the conventional t-plot method (*J. Catalysis,* 1965, 4, 319) (micropore volume by the t-plot method is 0.074 cc/gm).

What is claimed is:

1. A method for performing an acylation reaction on an aromatic substrate ArH$_n$ to form a product ArH$_{n-1}$COR, the method comprising the steps of:

providing the aromatic substrate, intimately mixing the substrate and an acylating agent, wherein the acylating agent is selected from the group consisting of a carboxylic acid derivative, a carboxylic acid, an acid anhydride, an ester, and an acyl halide, and exposing an intimate mixture thus formed to a catalyst comprising a molecular sieve having a mole ratio greater than about 15 of (1) silicon oxide to (2) an oxide selected from aluminum oxide, gallium oxide, iron oxide, boron oxide, titanium oxide, vanadium oxide and mixtures thereof and having, after calcination, the X-ray diffraction lines of Table II.

2. The method of claim 1 wherein the organic substrate is selected from the group consisting of benzene, toluene, anisole and 2-naphthol.

3. The method of claim 2 wherein the organic substrate is anisole.

4. The method of claim 1 wherein the acylating agent is selected from the group consisting of carboxylic acid derivatives, carboxylic acids, acid anhydrides, esters, and acyl halides.

* * * * *